(12) United States Patent
Pynson et al.

(10) Patent No.: US 6,599,280 B1
(45) Date of Patent: Jul. 29, 2003

(54) SURGICAL KIT FOR THE PREPARATION OF TAMPONADE GAS

(75) Inventors: Joel Pynson, Toulouse (FR); Florian David, Toulouse (FR)

(73) Assignee: Bausch & Lomb Incorporated, Rochester, NY (US)

( * ) Notice: Subject to any disclaimer, the term of this patent is extended or adjusted under 35 U.S.C. 154(b) by 75 days.

(21) Appl. No.: 09/693,522

(22) Filed: Oct. 20, 2000

(51) Int. Cl.[7] ............................................. A61B 19/00
(52) U.S. Cl. ..................................................... 604/403
(58) Field of Search ................................. 206/570, 363, 206/370, 440, 438, 564; 604/403

(56) References Cited

U.S. PATENT DOCUMENTS

| | | | | |
|---|---|---|---|---|
| 5,377,835 A | | 1/1995 | Cornelissen et al. | 206/455 |
| 5,390,792 A | | 2/1995 | Van Ness et al. | 206/439 |
| 5,392,917 A | * | 2/1995 | Alpern et al. | 206/570 |
| 5,507,279 A | * | 4/1996 | Fortune et al. | 128/200.26 |
| 5,554,097 A | * | 9/1996 | Guy | 600/102 |
| 5,699,909 A | * | 12/1997 | Foster | 206/370 |
| 5,779,053 A | * | 7/1998 | Partika | 206/570 |
| 6,073,759 A | | 6/2000 | Lamborne et al. | 206/213.1 |
| 6,412,639 B1 | * | 7/2002 | Hickey | 206/570 |

FOREIGN PATENT DOCUMENTS

WO     WO 98/45191     10/1998

* cited by examiner

*Primary Examiner*—Manuel Mendez
(74) *Attorney, Agent, or Firm*—Rita D. Vacca

(57) ABSTRACT

A surgical kit to prepare a unit dose injection of a surgical gas. The surgical kit includes a gas pouch filled with a surgical gas, a syringe with a needle and a plunger. Optionally additional product components are included in the surgical kit depending on the surgical procedure for which the kit is prepared, such as for example a sterilizing filter, a stopcock and a suspended spike. Preferably the surgical kit may be used in ophthalmic surgical procedures to prepare a unit dose of tamponade gas to repair retinal tears.

11 Claims, 5 Drawing Sheets

SURGICAL KIT FOR THE PREPARATION OF TAMPONADE GAS

FIELD OF THE INVENTION

The present invention relates generally to a surgical kit for the preparation of a surgical gas and a method of assembling and using the same. More specifically, the present invention relates to a surgical kit and the assembly and use thereof to provide a unit dose of tamponade gas to a patient during an ophthalmic surgical procedure.

BACKGROUND OF THE INVENTION

Syringes filled with a gas are useful in a number of surgical procedures requiring the injection of a gas bubble into a patient's body. One such surgical procedure requiring the injection of a gas bubble into a patient is that of repairing a retinal tear. A retinal tear can be treated using an injected gas bubble such as sulfur hexafluoride (SF6), perfluoroethane (C2F6) or perfluoropropane (C3F8) for gas tamponage. Another such surgical procedure is that of injecting carbon dioxide (CO2) gas into a blood vessel to facilitate percutaneous angioscopy. Still another such surgical procedure is that of using injections of nitric oxide (NO) gas and NO-releasing compounds to treat male impotence, inhibition of DNA synthesis and mitochondrial respiration in tumor cells, and to relax vascular smooth muscle for control of hypertension.

Gases used for such surgical procedures are often expensive and not available in ready-to-use unit dose form. Currently, surgical gases are purchased packaged in pressurized tanks. Syringes are filled directly from the tanks using a filling line. When a syringe is disconnected from the filling line, the gas remaining in the filling line is released into the atmosphere. Thus, this method of preparing syringes for surgery is not entirely desirable due to the significant amount of gas that is wasted. Additionally, due to the busy environment of a hospital, shut-off valves on surgical gas tanks are frequently left open accidentally causing an even greater amount of gas to be wasted than when syringes are being filled.

An even more serious problem than that of wasting expensive surgical gases, is that of gas dilution within the prepared syringe prior to surgery. Syringes are sometimes prepared on the morning of the day they are to be used in a surgical procedure. Once prepared, the syringes are placed in the operating room with other surgical devices until they are used, which can be several hours later. Experiments have shown that leakage of surgical gas from a syringe over a relatively short period of time can cause clinically significant dilution of the gas thereby increasing the risk of surgical complications. For instance, the concentration of sulfur hexafluoride in a plastic syringe has been observed to decrease from 97% at 30 seconds after aspiration to 76% at 60 minutes and 2% at 18 hours after aspiration.

In U.S. Pat. No. 6,073,759 a method of preparing a gas-filled syringe is disclosed which comprises filling a high gas barrier material container with a predetermined volume of a gas, puncturing the container with the syringe needle and drawing the gas into the syringe by retracting the syringe plunger. As taught, such a method is not entirely desirable due to complications associated with the need to maintain the gas-filled container at a pressure above atmospheric pressure.

In U.S. Pat. No. 5,390,792 packaging for protective sterile containment of a rigid product is disclosed. The packaging is designed to enable circulation of sterilizing fluids about the surface of the rigid product for improved and substantially unhindered circulation of sterilizing gases throughout the interior of the packaging. Such packaging is desirable for purposes of sterilization but is not suitable for packaging of surgical gases due to the characteristics of the breathable plastic cover film.

In U.S. Pat. No. 5,377,835 a reclosable film package is disclosed which is light-tight, air-tight and reclosable made from metallized polyester foil, lined with black polyethylene. A reclosable film package is not desirable in conjunction with the packaging of surgical gases due to the preference for single-use only products.

Because of the noted shortcomings of current packaging designs, there is a need for a surgical kit designed for the preparation and use of a unit dose of surgical gas.

SUMMARY OF THE INVENTION

The present invention provides a surgical kit for the preparation of a unit dose of a surgical gas, such as a tamponade gas for ophthalmic use, and a method of using the same. The product components of the subject kit are preferably provided in a sterile blister-type packaging structure formed from a rigid resiliently flexible thermoformed plastic container and a sealed cover therefor. The plastic container preferably has a plurality of indentations molded or thermoformed therein. The indentations form interior contacting surfaces shaped in correlation with the exterior surface dimensions of the product components housed in the container so as to position the product components therein in a specified orientation. The interior contacting surfaces likewise protectively maintain product components within the packaging structure in a fixed position during shipping and handling of the surgical kit so as to secure the same from potential damage due to impacts and/or shocks imparted during shipping and/or storage.

The preferred surgical kit of the present invention includes a gas pouch filled to approximately atmospheric pressure, such as within the range of approximately 0.95 to 1.05 atmospheres of pressure with a surgical gas, a syringe with plunger, a sterilizing filter, a stopcock, a suspended spike and a capped injection needle or cannula as product components. However, numerous product component variations may be included in the subject surgical kit, depending on the surgical procedure for which the kit is prepared, to provide for the preparation of a unit-dosage of gas for use in surgery.

The gas-filled syringe is prepared just before surgery by connecting the sterilizing filter, the stopcock and the suspended spike respectively to the syringe. The suspended spike is then used to perforate a plug positioned within a filling nozzle of the gas pouch. The desired volume of surgical gas is drawn into the syringe by withdrawing the plunger a specific distance from within the syringe interior as dictated by the volume desired. The stopcock is then closed to seal the gas pouch prior to removal of the syringe. A capped injection needle or cannula is then connected to the syringe for use in a surgical procedure. Alternatively, a syringe with a capped injection needle or cannula can be directly used to perforate the plug positioned within the filling nozzle of the gas pouch depending on the requirements of the specific surgical procedure.

If a gas/air mixture is desired for the surgical procedure, the syringe and the sterilizing filter are removed from the stopcock. To prepare a gas/air mixture, if desired, the desired volume of air is drawn into the syringe through the sterilizing filter by withdrawing the plunger a specific distance from within the syringe interior as dictated by the volume desired. The sterilizing filter is then removed from the syringe and the capped injection needle or cannula connected to the syringe for use in a surgical procedure.

Accordingly, it is an object of the present invention to provide a surgical kit for the preparation of a surgical gas.

Another object of the present invention is to provide a surgical kit for the preparation of a unit-dose of tamponade gas.

Another object of the present invention is to provide a surgical kit for the preparation of a unit-dose gas/air mixture.

Another object of the present invention is to provide a method of using product components of a surgical kit for the preparation of a tamponade gas.

Still another object of the present invention is to provide a method of using product components of a surgical kit for the preparation of a unit-dose gas/air mixture.

These and other objectives and advantages of the present invention, some of which are specifically described and others that are not, will bercome apparent from the drawings, detailed description and claims that follow.

DETAILED DESCRIPTION OF THE INVENTION

Figure 1:
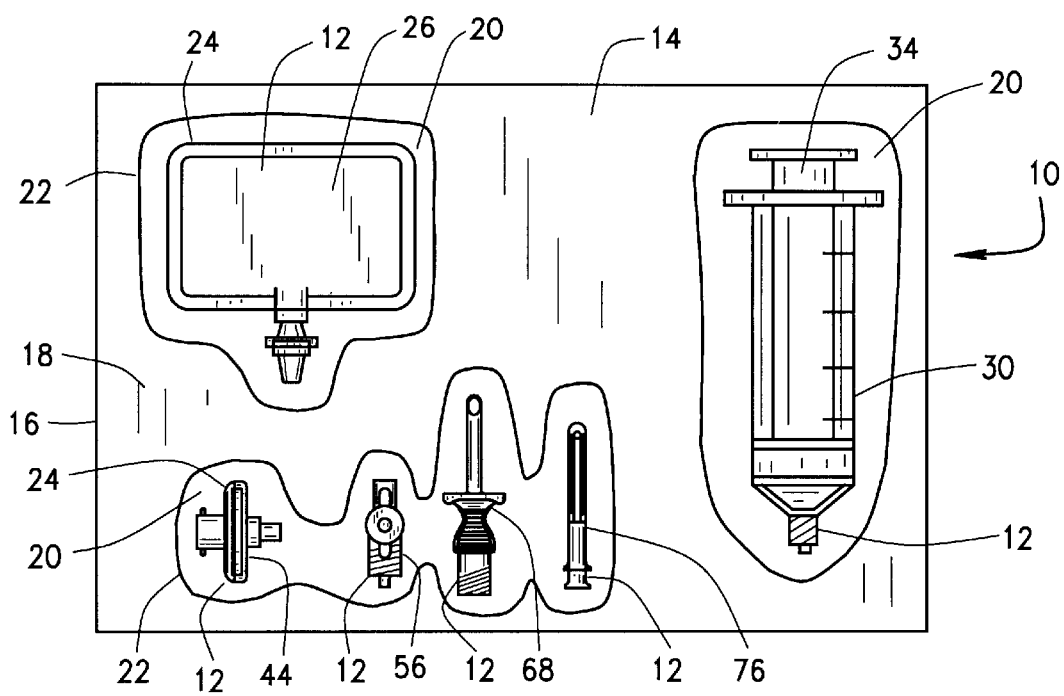
FIG. 1 is a plan view of a surgical kit made in accordance with the present invention.

The present surgical kit 10 is best illustrated in FIG. 1. Surgical kit 10 is preferably provided for the preparation of a unit dose ophthalmic tamponade gas injection. However, surgical kit 10 is likewise suitable for use in the preparation of other surgical gases 28 for use in other surgical procedures. Product components 12 of surgical kit 10 are preferably provided in a sterile blister-type packaging structure 14 formed from a rigid resiliently flexible thermoformed plastic container 16 and a non-permanently sealed cover 18 therefor. Packaging structure 14 is preferably suitably sized for convenience in use and storage. For this purpose, packaging structure 14 is ideally smaller than 20 inches by 20 inches and more preferably smaller than 12 inches by 12 inches although larger sizes could be used to accommodate the needs of a particular surgical procedure. Suitable materials for the manufacture of plastic container 16 include but are not limited to polypropylene, polyethylene terephthalate copolyester or polyvinyl chloride. Preferably plastic container 16 is manufactured from polyethylene terephthalate copolyester for purposes of environmental friendliness. Suitable materials for the manufacture of sealed cover 18 include but are not limited to a spun bonded olefin material such as Tyvek™ (Dupont, Wilmington, Del.), polypropylene, polyethylene terephthalate copolyester, polyvinyl chloride or coated paper such as PGL 70 or PGL 110. Preferably, sealed cover 18 is manufactured from coated paper for increased ease with respect to sterilization methods. Plastic container 16 is preferably molded or thermoformed to have a plurality of indentations 20 formed therein. Indentations 20 form interior contacting surfaces 22 shaped in correlation with the exterior surface dimensions 24 of product components 12 housed in plastic container 16 so as to position product components 12 therein in a specified orientation. The interior contacting surfaces 22 likewise protectively maintain product components 12 within the packaging structure 14 in a fixed position during shipping and handling of surgical kit 10 so as to secure the same from potential damage due to impacts and/or shocks imparted during shipping and/or storage. Sealed cover 18 may be planar or alternatively molded or thermoformed to have indentations 20 formed therein to correspond with those of plastic container 16. Plastic container 16 and sealed cover 18 are manufactured to be capable of being non-permanently sealed through the use of a suitable adhesive or by heat-sealing for the purpose of maintaining the sterility of product components 12 contained therein.

Product components 12 of surgical kit 10, as best illustrated in FIGS. 2 through 7, preferably include a gas pouch 26 filled to approximately atmospheric pressure such as within the range of approximately 0.95 to 1.05 atmospheres of pressure with a surgical gas 28, a syringe 30 with a plunger 34, a sterilizing filter 44, a stopcock 56, a suspended spike 68 and a capped injection needle 76. Optionally, a cannula could also be used in the present invention rather than capped injection needle 76. However, for purposes of simplicity, the present invention will be described in terms of using only a capped injection needle 76. Surgical kit 10 could likewise be customized such as by adding to product components 12, deleting from product components 12 or modifying product components 12 as desired to accommodate the requirements of particular surgical procedures during which a surgical gas 28 is used.

Figure 2:
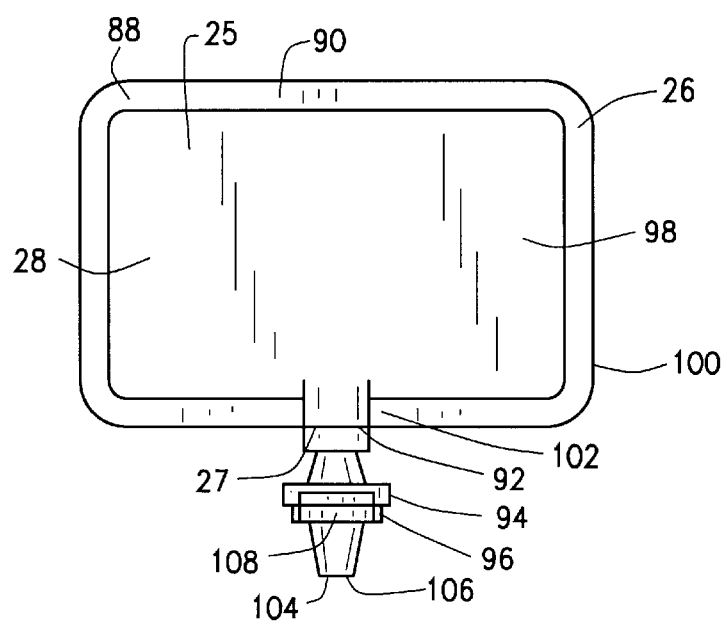
FIG. 2 is a plan view of the gas pouch product component of the surgical kit of FIG. 1.

The subject surgical kit 10 provides for the preparation of a unit-dosage of surgical gas 28 for use in a surgical procedure. The preferred surgical gas is provided in gas pouch 26. Gas pouch 26 illustrated in FIG. 2 is manufactured from a gas barrier material such as metal foils or metallized polymer laminates such as laminates having one or more metallized layers of nylon, oriented polypropylene, polyethylene, ethylene vinyl alcohol, polyethylene terephthalate, low density polyethylene, medium density polyethylene or cellophane. A lacquer or like coating can also be used to create a cold seal. Preferably, the present gas pouch 26 is manufactured from a laminar sheet of three materials of differing characteristics. The first material layer 88 forming the exterior 25 of gas pouch 26 is a 24-micrometer thick layer of polyester to provide the necessary mechanical strength to gas pouch 26. The second material layer 90 is adhered to first material layer 88 using a polyurethane bi-component adhesive. Second material layer 90 is a 12-micrometer thick layer of aluminum to provide a gas barrier and a light barrier. The third material layer 92 forming the interior 27 of gas pouch 26 is a 70-micrometer thick layer of polyethylene to provide the necessary ability to weld the materials together to form a permanently sealed pouch for containment of surgical gas 28. Sealed between interior 27 of anterior surface 98 and interior 27 of posterior surface 100 is a sealed end 102 of a filling nozzle 94. Filling nozzle 94 is preferably of tubular construction having an open passageway 106 in fluid communication with interior 27 of gas pouch 26 extending from sealed end 102 to free end 104. Located between sealed end 102 and free end 104 is valve portion 96. Valve portion 96 is constructed to have passageway 106 of a diameter greater than that of sealed end 102 and free end 104. Fixed within enlarged passageway 106 of valve portion 96 is a natural or synthetic rubber or rubber-like material gas barrier plug 108. Passageway 106 of free end 104 is dimensioned to accept a tubular spike 74 for perforation of gas barrier plug 108 as described in greater detail below. Surgical gases 28 that may be packaged in gas pouch 26 include but are not limited to sulfur hexafluoride, perfluoropropane, perfluoroethane, carbon dioxide, nitric oxide or nitric oxide releasing compounds but preferably sulfur hexafluoride, perfluoropropane or perfluoroethane for use a tamponade in ophthalmic surgical procedures. Gas pouch 26 is filled to approximately atmospheric pressure, such as within the range of approximately 0.95 to 1.05 atmospheres of pressure, with surgical gas 28 by using a form/fill/seal machine or by evacuation, filling with a selected gas and sealing. Gas pouch 26 is preferably filled to approximately atmospheric pressure to avoid condensation within gas pouch 26 and concomitant contamination. The volume of gas pouch 26 may vary depending on the requirements of the particular surgical procedure for which surgical kit 10 is tailored. Preferably, for purposes of providing tamponade gas for use in ophthalmic surgery to repair a retinal tear, the volume of gas pouch 26 is approximately 30 to 100 cubic centimeters and most preferably 50 to 60 cubic centimeters.

Figure 3:
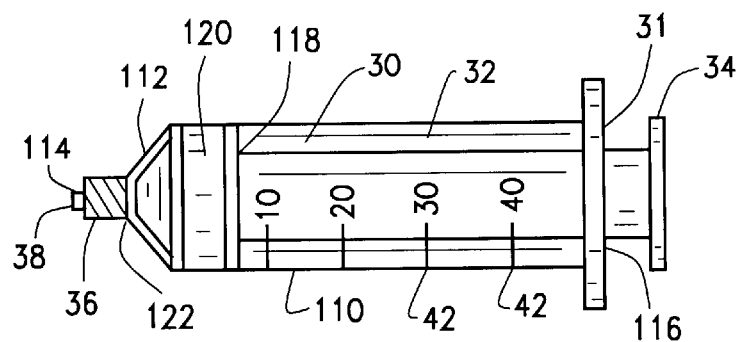
FIG. 3 is a plan view of the syringe product component of the surgical kit of FIG. 1.

Another product component 12 included in surgical kit 10 is a syringe 30. Syringe 30 as illustrated in FIG. 3 has a body portion 32 having a longitudinally cylindrical section 110, a frustoconical section 112 and a gas delivery outlet 114 with a gas dispensing tip 38 and a locking means 36, which are all preferably formed as an integral, unitary member. Body portion 32 can be formed from a material with a high degree of gas impermeability such as glass or one or more suitable polymers such as but not limited to polypropylene. Interior 31 of body portion 32 defines a passageway 116, which can be filled with one or more selected gases in a conventional manner. One or more gases may be retained within passageway 116 by plunger 34 and capped injection needle 76. Interior end 118 of plunger 34 proximal with respect to the frustoconical section 112 of body portion 32 can be provided with a stopper 120 dimensioned to slidably engage interior 31 of body portion 32 to controllably change the level of gas pressurization within passageway 116. Gas dispensing tip 38 is dimensioned for removable attachment of a sterilizing filter 44 or a capped injection needle 76. Formed around base periphery 122 of gas dispensing tip 38 are locking means 36 for removable attachment of sterilizing filter 44 or capped injection needle 76. Locking means 36 may take any of a variety of forms known to those skilled in the art such as but not limited to threads, one or more spaced tabs or one or more spaced grooves but preferably threads. Preferably volume indicia 42 is likewise provided on body portion 32 for ease in using syringe 30 to provide a unit dose of surgical gas 28.

Figure 4:
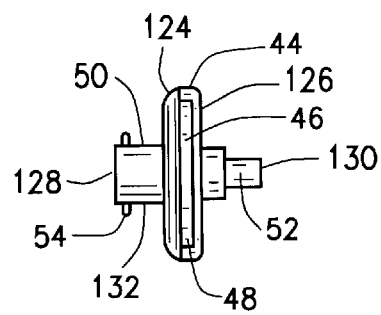
FIG. 4 is a plan view of the sterilizing filter product component of the surgical kit of FIG. 1.

Another product component 12 included in surgical kit 10, which may be optional depending on surgical procedure, is sterilizing filter 44 as illustrated in FIG. 4. Sterilizing filter 44 is formed from any suitable material including but not limited to polypropylene or polyvinyl chloride but preferably polyvinyl chloride. Sterilizing filter 44 preferably comprises two permanently connected housing members 124 and 126 with two opposed tubular extensions 50 and 52 respectively extending therefrom. Protruding from the exterior surface 132 of tubular extension 50 is one or more flange locking means 54. Flange locking means 54 are proportioned to be accepted by locking means 36 of syringe 30 for non-permanent attachment thereto. Tubular extension 52 is proportioned to be accepted within passageway 60 of stopcock 56 and non-permanently attached therein by friction fit. Connected housing members 124 and 126 form a cavity 46 in fluid communication with passages 128 and 130 of tubular extensions 50 and 52 respectively. Within cavity 46 is a bacterial and microbial barrier material 48 such as but not limited to polyvinylidene fluoride or polytetrafluoroethylene but preferably polyvinylidene fluoride. Sterilizing filter 44 is used to ensure sterility of any surgical gas 28 or gases drawn within syringe 30.

Figure 5:
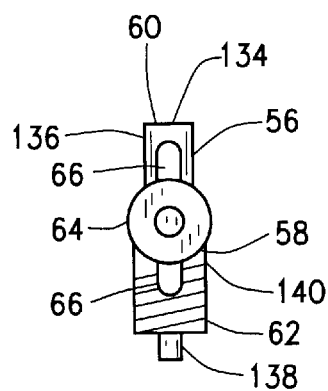
FIG. 5 is a plan view of the stopcock product component of the surgical kit of FIG. 1.

Another product component 12 of surgical kit 10, which may be optional depending on surgical procedure, is stopcock 56 as illustrated in FIG. 5. Stopcock 56 is formed from any suitable material such as but not limited to polycarbonate/acetal or polycarbonate but preferably polycarbonate. Stopcock 56 comprises a tubular member 58 having two opposed free ends 136 and 138 and an interior 134 defining a passageway 60 therethrough. Tubular member 58 has a valve member 64 equipped with a valve handle 66. Valve member 64 extends through tubular member 58 between opposed free ends 136 and 138. Upon parallel alignment of valve handle 66 with regard to tubular member 58, valve member 64 allows fluid flow through tubular member 58. Upon perpendicular alignment of valve handle 66 with regard to tubular member 58, fluid flow through tubular member 58 is blocked. Free end 136 is dimensioned for removable friction fit attachment of a sterilizing filter 44. Formed around base periphery 140 of free end 138 are locking means 62 for removable attachment of a suspended spike 68. Locking means 62 may take any of a variety of forms known to those skilled in the art such as but not limited to threads, one or more spaced tabs or one or more spaced grooves but preferably threads.

Figure 6:
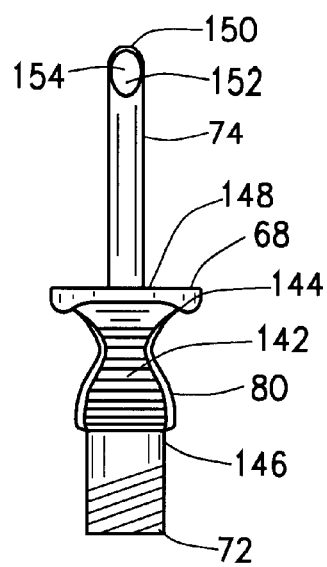
FIG. 6 is a plan view of the suspended spike product component of the surgical kit of FIG. 1.

Another product component 12 of surgical kit 10, which may be optional depending on surgical procedure, is a suspended spike 68 as illustrated in FIG. 6. Suspended spike 68 may be manufactured from any suitable material such as but not limited to acrylonitrile butadiene styrene terpolymer or polyethylene but preferably acrylonitrile butadiene styrene terpolymer. Suspended spike 68 comprises a tubular body portion 80 having two opposed free ends 146 and 148, gripping means 142 and flange portion 144. Preferably gripping means 142 are formed by a series of ridges to increase friction and aid handling. Other suitable methods of increasing the friction of gripping means 142 include but are not limited to a plurality of raised knobs or buttons or a coating of natural or synthetic rubber or rubber-like material. Flange portion 144 is provided to allow a user to abut one's fingers there against to aid in forcing elongated tubular spike 74 through gas barrier plug 108 or the like. Extending from free end 146 are tubular locking means 72, which may take any of a variety of forms known to those skilled in the art such as but not limited to threads, one or more spaced tabs or one or more spaced grooves but preferably threads. Tubular locking means 72 is dimensioned for non-permanent attachment to free end 138 of stopcock 56. Extending from free end 148 of suspended spike 68 is elongated tubular spike 74 having a sharpened tip 150. Passageway 152 is defined by interior surfaces 154 of tubular spike 74, tubular body portion 80 and tubular locking means 72 for fluid communication therethrough.

Figure 7:
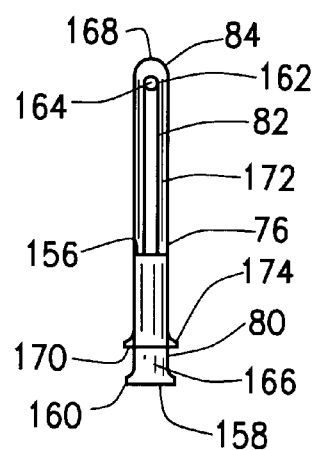
FIG. 7 is a plan view of the capped injection needle product component of the surgical kit of FIG. 1.

Still another product component 12 of surgical kit 10 is capped injection needle 76 as illustrated in FIG. 7. Capped injection needle 76 comprises a tubular body portion 80, a tubular needle 82 and a cap 84. Tubular body portion 80 has two opposed ends 156 and 158. Tubular needle 82 is permanently attached to end 156. Interior 162 defines passageway 164 that allows fluid communication through tubular needle 82 and body portion 80. Extending from end 158 are locking means 160, which may take any of a variety of forms known to those skilled in the art such as but not limited to a flange, threads, one or more spaced tabs or one or more spaced grooves but preferably a flange. Cap 84 is tubular having a closed end 168 and an opposed open end 170. Interior 174 of cap 84 defines a cavity 172 dimensioned to envelop tubular needle 82 and non-permanently attach by friction fit of open end 170 to exterior surface 166 of body portion 80.

Product components 12 are sterile in non-permanently sealed packaging structure 14 to facilitate the sterile transfer of product components 12 from packaging structure 14 into a sterile environment such as a surgical operating room. The interior of packaging structure 14 and product components 12 non-permanently sealed therein may be sterilized using one of a variety of methods known to those skilled in the art such as but not limited to exposure to sterilizing gases, radiation or the like.

Figure 8:
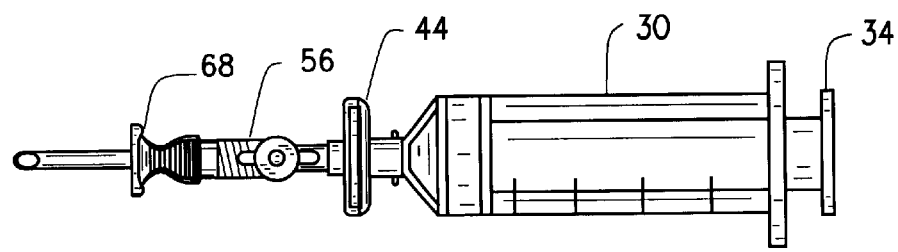
FIG. 8 is a plan view of the assembled syringe, sterilizing filter, stopcock and suspended spike product components of the surgical kit of FIG. 1.
Figure 9:
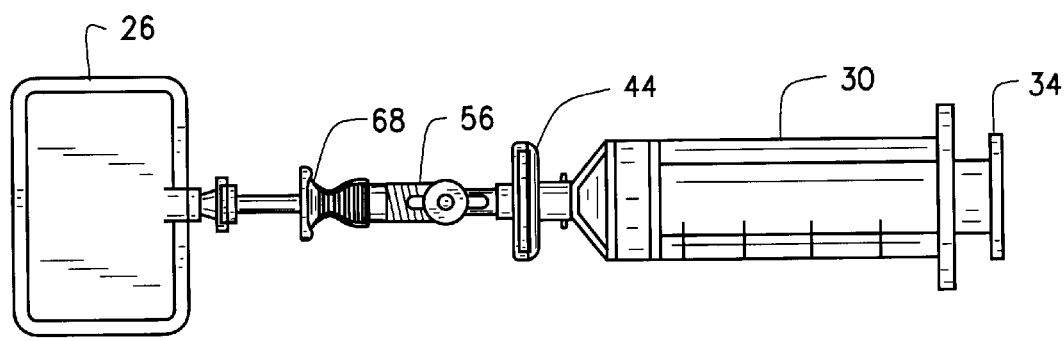
FIG. 9 is a plan view of the assembled syringe, sterilizing filter, stopcock, suspended spike and gas pouch product components of the surgical kit of FIG. 1.
Figure 10:
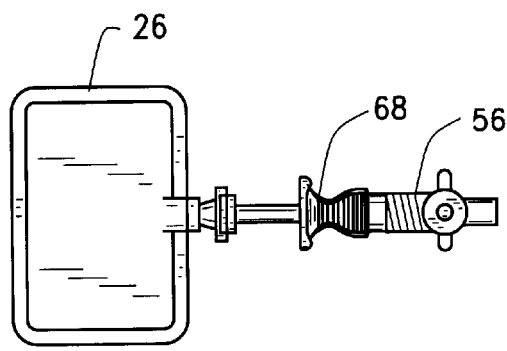
FIG. 10 is a plan view of the assembled gas pouch, suspended spike and stopcock product components of the surgical kit of FIG. 1.
Figure 11:
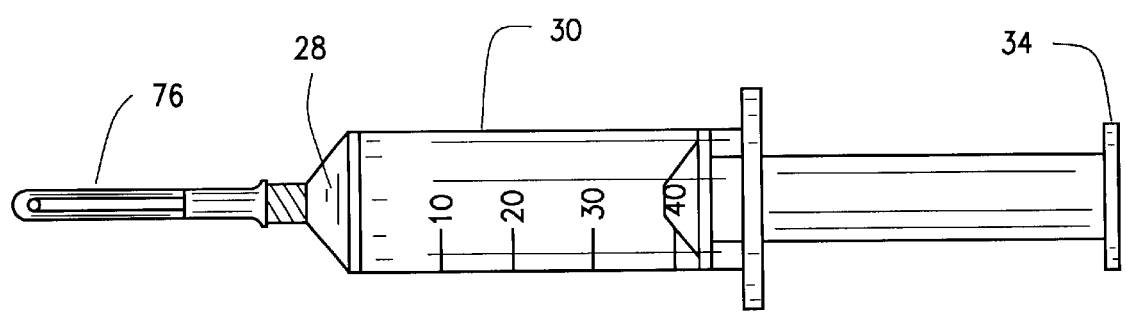
FIG. 11 is a plan view of the assembled syringe and capped injection needle product components of the surgical kit of FIG. 1.

Surgical kit 10 is used in a surgical procedure by preparing syringe 30. Syringe 30 is prepared by filling the same with surgical gas 28 just before the surgical procedure by removing cover 18 from container 16, removing necessary product components 12 from container 16 and connecting sterilizing filter 44, stopcock 56 and suspended spike 68 respectively to syringe 30 as illustrated in FIG. 8. Suspended spike 68 is then used to perforate gas barrier plug 108 as illustrated in FIG. 9. The desired volume of surgical gas 28 is drawn into syringe 30 by withdrawing plunger 34 from interior 31 of body portion 32 as necessary to achieve the desired volume. Stopcock 56 is then manipulated to block fluid flow by rotating valve handle 66 ninety degrees so as to be perpendicular with respect to tubular portion 58. If a gas/air mixture is desired, syringe 30 and non-permanently attached sterilizing filter 44 are then removed from stopcock 56 as illustrated in FIG. 10. The desired volume of air is drawn into syringe 30 through sterilizing filter 44 by withdrawing plunger 34 from interior 31 of body portion 32 as necessary to achieve the desired volume. Sterilizing filter 44 is then removed from prepared syringe 86 and capped injection needle 76 is connected to prepared syringe 86 for use in a surgical procedure as illustrated in FIG. 11. If a gas/air mixture is not desired, syringe 30 is removed from sterilizing filter 44 following filling with surgical gas 28 and connected to capped injection needle 76 for use in a surgical procedure. Alternatively, depending on the requirements of the surgical procedure, syringe 30 with connected capped injection needle 76 may be used by removing cap 84 to perforate gas barrier plug 108 and directly fill syringe 30 with surgical gas 28 as described above.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. A surgical kit for the preparation of a unit dose injection of a surgical gas comprising:

a syringe with a needle or cannula and a plunger;

a gas pouch equipped with a gas barrier plug and filled to approximately atmospheric pressure with a surgical gas;

and a non-permanently sealable packaging structure sized for containment of said syringe and said gas pouch therein.

2. The surgical kit of claim 1 including within said packaging structure a stopcock.

3. The surgical kit of claim 1 including within said packaging structure a sterilizing filter.

4. The surgical kit of claim 1 including within said packaging structure a suspended spike.

5. The surgical kit of claim 1 including within said packaging structure a stopcock, a sterilizing filter and a suspended spike.

6. The surgical kit of claim 1 wherein said gas pouch is filled to approximately atmospheric pressure with a surgical gas.

7. The surgical kit of claim 1 wherein said surgical gas is selected from the group consisting of sulfur hexafluoride, perfluoropropane, perfluoroethane, nitric oxide, and nitric oxide producing compounds.

8. The surgical kit of claim 1 wherein said surgical gas is sulfur hexafluoride, perfluoropropane or perfluoroethane for use as a tamponade in an ophthalmic surgical procedure.

9. The surgical kit of claim 1 wherein said surgical gas is sulfur hexafluoride, perfluoropropane or perfluoroethane for use as a tamponade in an ophthalmic surgical procedure to repair retinal tears.

10. The surgical kit of claim 1 wherein said gas pouch is manufactured from a laminar sheet formed from three materials of differing characteristics.

11. The surgical kit of claim 1 wherein said gas pouch is manufactured from a laminar sheet comprising a polyester layer, an aluminum layer and a polyethylene layer.

* * * * *